Figure 1:
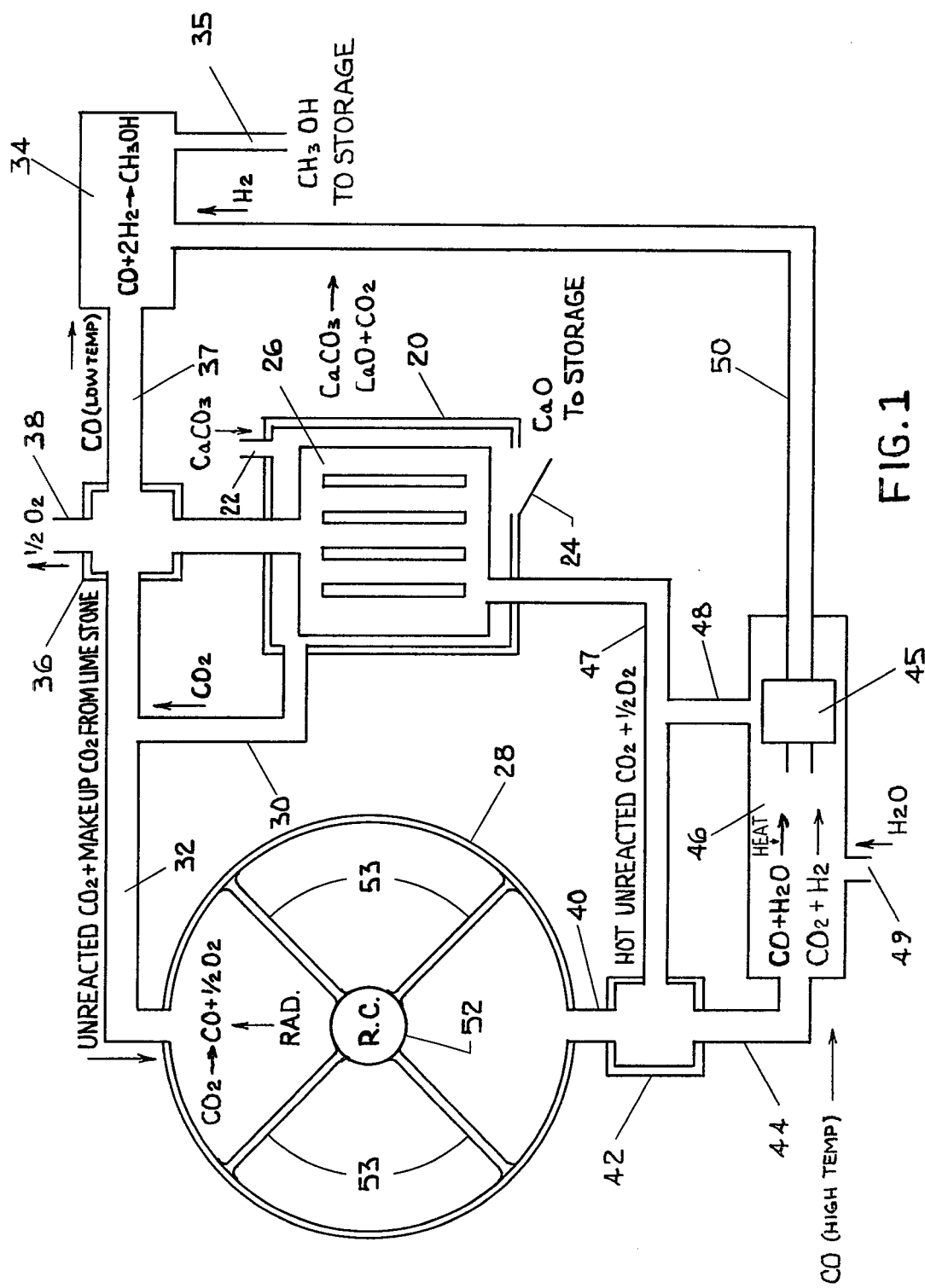

United States Patent [19]

Gomberg

[11] 4,132,727
[45] Jan. 2, 1979

[54] METHOD AND APPARATUS FOR THE MANUFACTURE OF METHANOL

[75] Inventor: Henry J. Gomberg, Ann Arbor, Mich.

[73] Assignee: Texas Gas Transmission Corporation, Owensboro, Ky.

[21] Appl. No.: 675,137

[22] Filed: Apr. 8, 1976

Related U.S. Application Data

[63] Continuation of Ser. No. 478,877, Jun. 7, 1974, abandoned.

[51] Int. Cl.² .......................... B01J 1/10; C07C 29/16
[52] U.S. Cl. .......................... 260/449.5; 204/157.1 H; 250/527
[58] Field of Search ................. 204/158 HE, 157 HE; 250/527; 260/449.5

[56] References Cited

U.S. PATENT DOCUMENTS

| 1,681,750 | 8/1928 | Storch | 260/449.5 |
| 3,378,446 | 4/1968 | Whittlesey | 176/1 |

OTHER PUBLICATIONS

Steinberg, Advances in Science & Technology, vol. 1 (1962), pp. 309, 312 & 313.

*Primary Examiner*—Howard S. Williams
*Attorney, Agent, or Firm*—Laurence R. Brown

[57] ABSTRACT

A Method and Apparatus for the Manufacture of Methanol ($CH_3OH$) in connection with a fusion reaction chamber which comprises utilizing the heat of fusion reaction to dissociate calcium carbonate $CaCO_3$ into CaO and $CO_2$. The resulting $CO_2$ is introduced into a fusion reaction chamber and subjected to heat and radiation which creates CO and $O_2$. The CO is mixed with water under conditions to create $CO_2$ and hydrogen. The hydrogen may then be combined with CO to form methanol and the $CO_2$ is utilized in a recycling system which feeds back into the reactor.

5 Claims, 2 Drawing Figures

1

METHOD AND APPARATUS FOR THE MANUFACTURE OF METHANOL

This is a continuation of application Ser. No. 478,877, filed June 7, 1974, now abandoned.

This invention relates to a Method and Apparatus for the Production of Methanol and more particularly to the production of methanol from an inorganic source of carbon.

In a copending application of Theodor Teichmann, Henry J. Gomberg and Robert J. Teitel, Ser. No. 414,367, filed Nov. 9, 1973, now abandoned, there is disclosed the concept of treatment of calcium carbonate with heat from a fusion reactor to break it down into $CO_2$ and lime (CaO). The present invention relates to the use of a fusion reactor in a system wherein calcium carbonate is dissociated and the resulting $CO_2$ is also broken down into carbon monoxide and oxygen. The system using the heat and radiation of a fusion reactor also proceeds in the production of hydrogen so that the carbon monoxide and hydrogen can be combined to form the desired product, methanol, $CH_3OH$.

The general character and construction of reaction chambers is described in the following U.S. patents:
  U.S. Pat. No. 3,378,446, Whittlesey, Apr. 16, 1968;
  U.S. Pat. No. 3,489,645, Daiber, Jan. 13, 1970;
  U.S. Pat. No. 3,624,239, Fraas, Nov. 30, 1971;
  U.S. Pat. No. 3,762,992, Hedstrom, Oct. 2, 1973;

It is therefore an object of the present invention to provide a system and apparatus for efficiently producing methanol utilizing an inorganic and plentiful source of carbon. It is a further object to utilize the heat and radiation of a fusion reaction to produce simultaneously the components for methanol which can then be readily formed. It is a further object to provide a system wherein certain of the products are recycled thus making it possible to add continuously only a make-up quantity of the raw material. A further object is the formation of used by-products, lime and oxygen, as well as the desired product, methanol.

Other objects and features of the invention will be apparent in the following description and claims in which is set forth the principles of the invention and the best mode presently contemplated for the practice of the same.

Drawings accompany the disclosure and the various views thereof may be briefly described as:
  FIG. 1, a reaction chamber and a diagrammatic flow system showing the process; and
  FIG. 2, a longitudinal section of the reaction and radiation chamber.

The basic methanol cycle is as follows:

$$CO + 2H_2 \rightarrow CH_3OH$$

To obtain carbon monoxide from an inorganic source, such as calcium carbonate, the following will pertain:

$$CaCO_3 \xrightarrow{heat} CaO\ (lime) + CO_2$$

$$CO_2 + radiation \rightarrow CO + \tfrac{1}{2} O$$

Then:

$$H_2O + CO \rightarrow CO_2 + H_2$$

$$CO + 2H_2 \rightarrow CH_3OH\ (Methanol)$$

For accomplishing the cycle in accordance with the present invention, the following cycle is preferred. It involves the use of five storage bins and suitable connections and pumps to feed in and out of such bins.

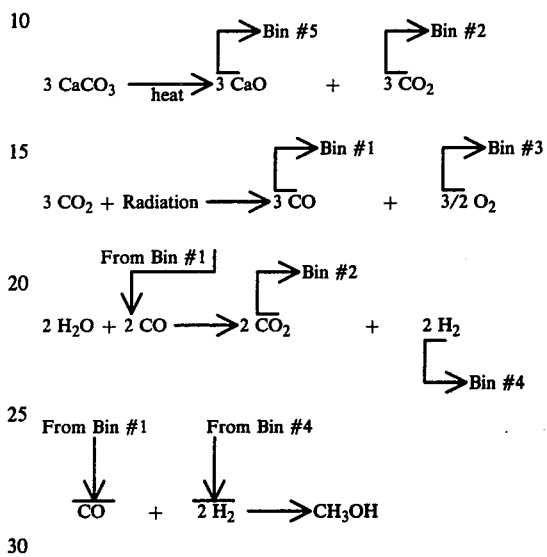

Figure 2:
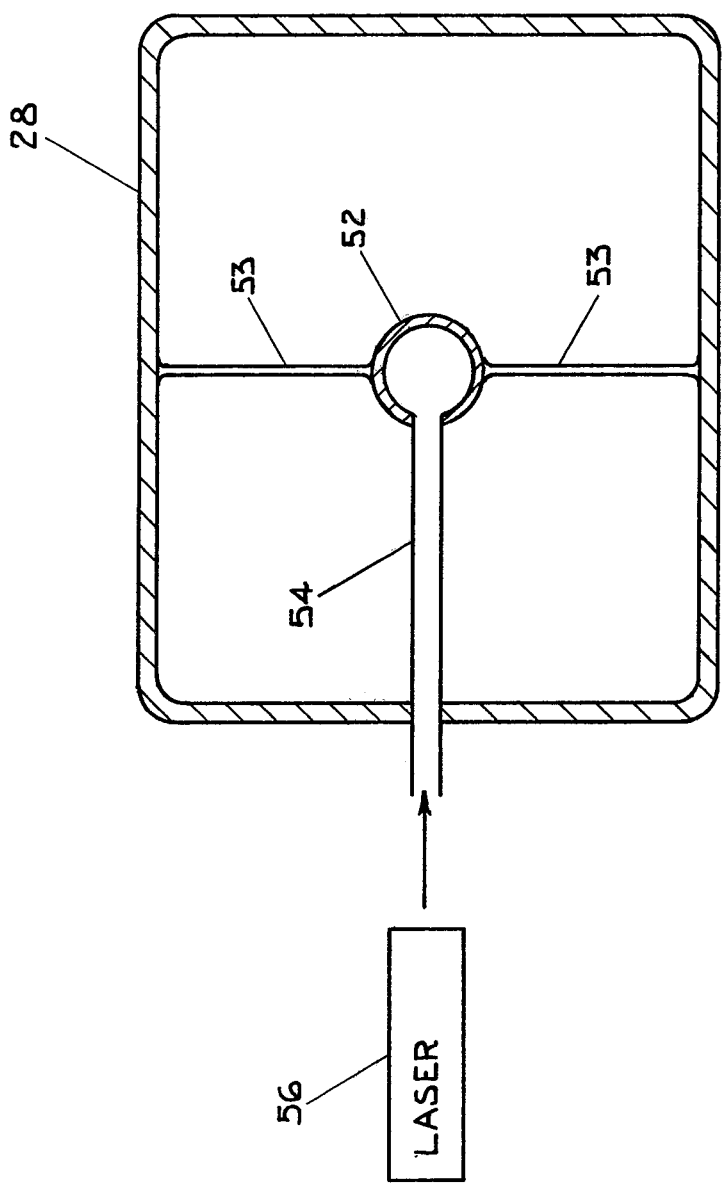

In connection with the accompanying drawings, FIGS. 1 and 2, the system starts with a roasting chamber 20 with an inlet hatch 22 and an outlet hatch 24. In a continuous process a suitable conveyor may be used to convey the material through chamber 20. Heat is furnished to the chamber by a heater 26 which receives hot gases from a fusion reactor containment chamber 28. The chamber 20 is connected to a conduit 30 leading to a cross-conduit 32 between reactor chamber 28 and a chemical reaction chamber 34. A separator 36 is provided at the intersection of the heating line 28 and the cross-conduit to distribute oxygen to a by-pass conduit 38 and separate unreacted $CO_2$ and carbon monoxide (CO). This separation can be accomplished by using the known processes described in U.S. patents to Schmid U.S. Pat. No. 3,594,986 (1971); Billings U.S. Pat. No. 3,658,463 (1972); Wallace U.S. Pat. No. 3,712,025 (1973); and Merriman et al U.S. Pat. No. 3,762,133 (1973).

Leading from the reaction chamber 28 is a conduit 40 leading to a separator 42 which discharges CO into a conduit 44 leading to a chamber 46, and which discharges $CO_2 + \tfrac{1}{2} O_2$ into a conduit 47 leading to the heating coil 26. This separator 42 operates in the same manner as separator 36 above described. A conduit 48 leads off from chamber 46 to intercept conduit 47 and an outlet conduit 50 connects chamber 46 to chemical reaction chamber 34.

The containment chamber 28 is formed of a thermal and radiation barrier material and has a laser fusion reaction chamber 52 suitably supported by rods 53 centrally thereof. Chambers of this nature are described in the previously referenced patents to Daiber, Whittlesey, Fraas and Hedstrom.

A laser tube 54 projects into chamber 28 from a laser 56 with prescribed output to create a fusion reaction when directed to suitably positioned laser fuel. Heat and radiation will fill the chamber 28 which is of proper size in relation to the neutron absorption length.

In the operation of the system, a suitable supply of calcium carbonate is introduced into the roasting chamber 20 through the hatch opening 22. The heat from the heat exchanger 26 drives off $CO_2$ leaving CaO (lime) which is moved out of the chamber through outlet hatch 24. A continuous conveyor system could readily be utilized in this part of the apparatus. Carbon dioxide gas passes from chamber 20 through pipe 30 to conduit 32 where it mixes with unreacted $CO_2$ when the process is in continuous cycle. This $CO_2$ gas enters the reaction chamber 28 where it is exposed to radiation as a result of the firing of the fusion fuel in the reaction chamber 52.

The radiation exposure results in the dissociation of carbon dioxide into carbon monoxide and oxygen in the reaction:

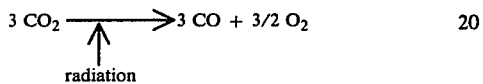

$$3\ CO_2 \longrightarrow 3\ CO + 3/2\ O_2$$
$$\uparrow$$
$$\text{radiation}$$

The hot gases are moved by suitable pumping apparatus into pipe 40 and to a separator 42. Separated CO is carried through pipe 44 to a reaction chamber 46 into which water is introduced through passage 49 in the form of steam. The reaction of CO and $H_2O$ with the addition of heat produces $CO_2$ and hydrogen ($H_2$). A suitable separator device 45 is provided so that the hydrogen is taken off into pipe 50 leading to chamber 34 and the resulting $CO_2$ is diverted through pipe 48 to a pipe 47 which is already receiving hot unreacted gases $CO_2$ and $O_2$ and some CO from separator 42. The separation at chamber 45 at the right hand end of chamber 46 can be accomplished by the known processes described in U.S. patents to Betterridge U.S. Pat. No. 3,406,496 (1968); Kurata U.S. Pat. No. 3,616,600 (1971); Smith U.S. Pat. No. 3,618,331 (1971); and Bratzler U.S. Pat. No. 3,653,810 (1972).

The hot unreacted $CO_2$ and oxygen and some of the CO (which has resulted from the reaction in chamber 28) in pipe 47 are moved through the heat exchanger 26 to furnish heat to the chamber 20 and are moved thence to a separator 36 where the oxygen is taken off to a pipe 38 and a portion of the $CO_2$ is moved into pipe 32 to restart the cycle. Another residual portion of the gas from the heat exchanger, namely carbon monoxide, is also separated at 36 and moved to reaction chamber 34 where it reacts with hydrogen to form methanol in the reaction:

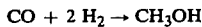

$$CO + 2\ H_2 \rightarrow CH_3OH$$

The methanol can be removed through a pipe 35 to a storage container.

When the apparatus is cycling on a continuous basis, the calcium carbonate is utilized simply to replenish the $CO_2$ supply since a portion of the $CO_2$ resulting from the radiative dissociation is recycled. The by-products are lime and oxygen.

I claim:

1. A method of making methanol which comprises the following simultaneous and continuous steps:
    (a) providing an initial source of $CO_2$;
    (b) introducing said $CO_2$ into a chamber;
    (c) subjecting said $CO_2$ in the chamber to heat and radiation to form hot gases CO and $O_2$;
    (d) utilizing some of said hot gases to heat a carbonate to form $CO_2$ for introduction into said chamber;
    (e) conducting CO gas from said chamber to a first mixing chamber;
    (f) introducing $H_2O$ into said mixing chamber to form $CO_2$ and $H_2$;
    (g) conducting the $H_2$ to a second mixing chamber; and
    (h) conducting a quantity of said hot gases to a separator where CO is separated and directing said CO to said second mixing chamber to form $CH_3OH$.

2. A method as defined in claim 1 carried out in a fusion reaction chamber supplying said heat and radiation, which includes the step of separating said hot gases utilized to heat said carbonate into unreacted $CO_2$, $O_2$ and CO, and directing said $CO_2$ to the chamber to supplement the initial source of $CO_2$.

3. A method as defined in claim 1 wherein said step of subjecting said $CO_2$ in the chamber to heat and reaction comprises the step of initiating a fusion reaction in said chamber.

4. An apparatus for making methanol which comprises:
    (a) a heat exchange chamber;
    (b) means for introducing a carbonate into said chamber;
    (c) a heat and radiation chamber;
    (d) means for transferring hot gases from said heat and radiation chamber to said heat exchange chamber;
    (e) a mixing chamber;
    (f) means to introduce CO from said heat and radiation chamber to said mixing chamber;
    (g) means to introduce $H_2O$ to said mixing chamber;
    (h) means to direct resulting $H_2$ to a second mixing chamber; and
    (i) means to introduce CO from said hot gases to said second mixing chamber to cause the formation of $CH_3OH$.

5. Apparatus as defined in claim 4 wherein said heat and radiation chamber comprises a fusion reactor chamber in which said hot gases are developed from a fusion reaction.

* * * * *